United States Patent [19]

Telang

[11] Patent Number: 5,382,244

[45] Date of Patent: Jan. 17, 1995

[54] STAND ALONE CONTROL MODULE

[75] Inventor: Anil M. Telang, Saugus, Calif.

[73] Assignee: Baxter International Inc., Deerfield, Ill.

[21] Appl. No.: 660,386

[22] Filed: Feb. 25, 1991

[51] Int. Cl.[6] ............................................. A61M 1/00
[52] U.S. Cl. ................................... 604/319; 604/317;
  604/321; 604/119
[58] Field of Search .......................... 604/46, 317–326,
  604/118–121; 220/400, 500, 501

[56] References Cited

U.S. PATENT DOCUMENTS

| Re. 29,877 | 1/1979 | Kurtz et al. . | |
|---|---|---|---|
| 3,363,627 | 1/1968 | Bidwell et al. . | |
| 3,683,913 | 8/1972 | Kurtz et al. | 604/319 X |
| 3,783,870 | 1/1974 | Schachet . | |
| 3,866,608 | 2/1975 | Reynolds et al. . | |
| 3,896,733 | 7/1975 | Rosenberg . | |
| 3,993,067 | 11/1976 | Schachet et al. | 604/9 X |
| 4,006,745 | 2/1977 | Sorenson et al. . | |
| 4,014,329 | 3/1977 | Welch et al. . | |
| 4,015,603 | 4/1977 | Kurtz et al. . | |
| 4,018,224 | 4/1977 | Kurtz et al. . | |
| 4,033,345 | 7/1977 | Sorenson et al. | 604/4 |
| 4,047,526 | 9/1977 | Reynolds et al. . | |
| 4,058,123 | 11/1977 | May . | |
| 4,105,031 | 8/1978 | Kurtz et al. . | |
| 4,111,204 | 9/1978 | Hessel | 604/320 X |
| 4,112,947 | 9/1978 | Nehring . | |
| 4,112,948 | 9/1978 | Kurtz et al. . | |
| 4,112,949 | 9/1978 | Rosenthal et al. . | |
| 4,195,633 | 4/1980 | Nehring et al. | 604/320 X |
| 4,278,089 | 7/1981 | Huck et al. . | |
| 4,289,158 | 9/1981 | Nehring . | |
| 4,296,748 | 10/1981 | Kurtz et al. . | |
| 4,347,946 | 9/1982 | Nichols | 604/319 X |
| 4,356,823 | 11/1982 | Jackson | 604/319 |
| 4,419,093 | 12/1983 | Deaton . | |
| 4,425,125 | 1/1984 | Kurtz et al. . | |
| 4,439,189 | 3/1984 | Sargeant et al. . | |
| 4,439,190 | 3/1984 | Protzmann et al. | 604/319 |
| 4,443,220 | 4/1984 | Hauer et al. . | |
| 4,445,884 | 5/1984 | Kurtz et al. . | |
| 4,453,937 | 6/1984 | Kurtz et al. . | |
| 4,465,483 | 8/1984 | Weilbacher . | |
| 4,468,226 | 8/1984 | Kurtz et al. . | |
| 4,469,484 | 9/1984 | Kurtz et al. . | |
| 4,484,908 | 11/1984 | Kurtz et al. . | |
| 4,487,606 | 12/1984 | Leviton et al. . | |
| 4,500,308 | 2/1985 | Kurtz et al. . | |
| 4,507,120 | 3/1985 | Paradis . | |

(Listed continued on next page.)

*Primary Examiner*—Randall L. Green
*Assistant Examiner*—Elizabeth M. Burke
*Attorney, Agent, or Firm*—Kay H. P. Hannafan; Paul C. Flattery

[57] ABSTRACT

A stand-alone control module for use in closed-wound drainage systems is described. The control module transforms a variable high-vacuum source into a constant low-vacuum source. The control module also provides a one-way check valve to prevent return of air to a patient when draining such air from the pleural cavity of the patient. The control module is a water-based control module. It includes a first-suction control chamber for transforming a variable high-vacuum into a constant low-vacuum. The first chamber contains a first column of fluid at a first pre-determined level. The module also includes a second water seal chamber that contains a second column of fluid at a second pre-determined level. The height of the second column of fluid is less than the height of the first column of fluid. Tubes are placed in each chamber that have one end of each tube located below the columns of fluid. The column of fluid within the first chamber acts to regulate the vacuum within the chambers and the column of fluid in the second chamber provides a one-way check valve to prevent air from returning to the patient.

9 Claims, 9 Drawing Sheets

U.S. PATENT DOCUMENTS

| | | |
|---|---|---|
| 4,515,283 | 5/1985 | Suzuki . |
| 4,516,973 | 5/1985 | Telang . |
| 4,519,796 | 5/1985 | Russo ............................. 604/319 |
| 4,522,623 | 6/1985 | Lauterjung . |
| 4,540,413 | 9/1985 | Russo . |
| 4,544,370 | 10/1985 | Elliott et al. . |
| 4,564,359 | 1/1986 | Ruhland . |
| 4,573,992 | 3/1986 | Marx . |
| 4,578,060 | 3/1986 | Huck et al. . |
| 4,619,647 | 10/1986 | Kurtz et al. .................. 604/319 X |
| 4,631,050 | 12/1986 | Reed et al. . |
| 4,650,477 | 3/1987 | Johnson . |
| 4,772,256 | 9/1988 | Lane et al. . |
| 4,781,707 | 11/1988 | Boehringer et al. . |
| 4,798,578 | 1/1989 | Ranford . |
| 4,838,872 | 6/1989 | Sherlock . |
| 4,846,800 | 7/1989 | Ouriel et al. ................. 604/319 X |
| 4,857,042 | 8/1989 | Schneider . |
| 4,898,572 | 2/1990 | Surugue nee Lasnier et al. . |
| 4,909,780 | 3/1990 | Ouriel et al. ................. 604/319 X |
| 4,923,438 | 5/1990 | Vasconcellos et al. . |
| 4,963,135 | 10/1990 | Kerwin . |
| 5,019,060 | 5/1991 | Goosen ............................. 604/319 |
| 5,149,325 | 9/1992 | Telang et al. ................. 604/319 X |

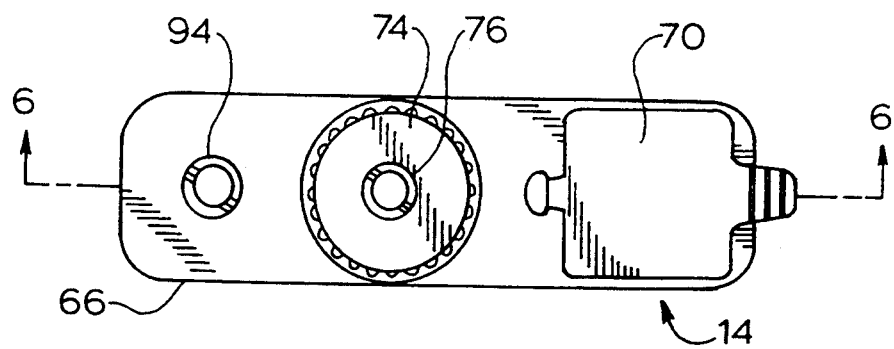
FIG. 7
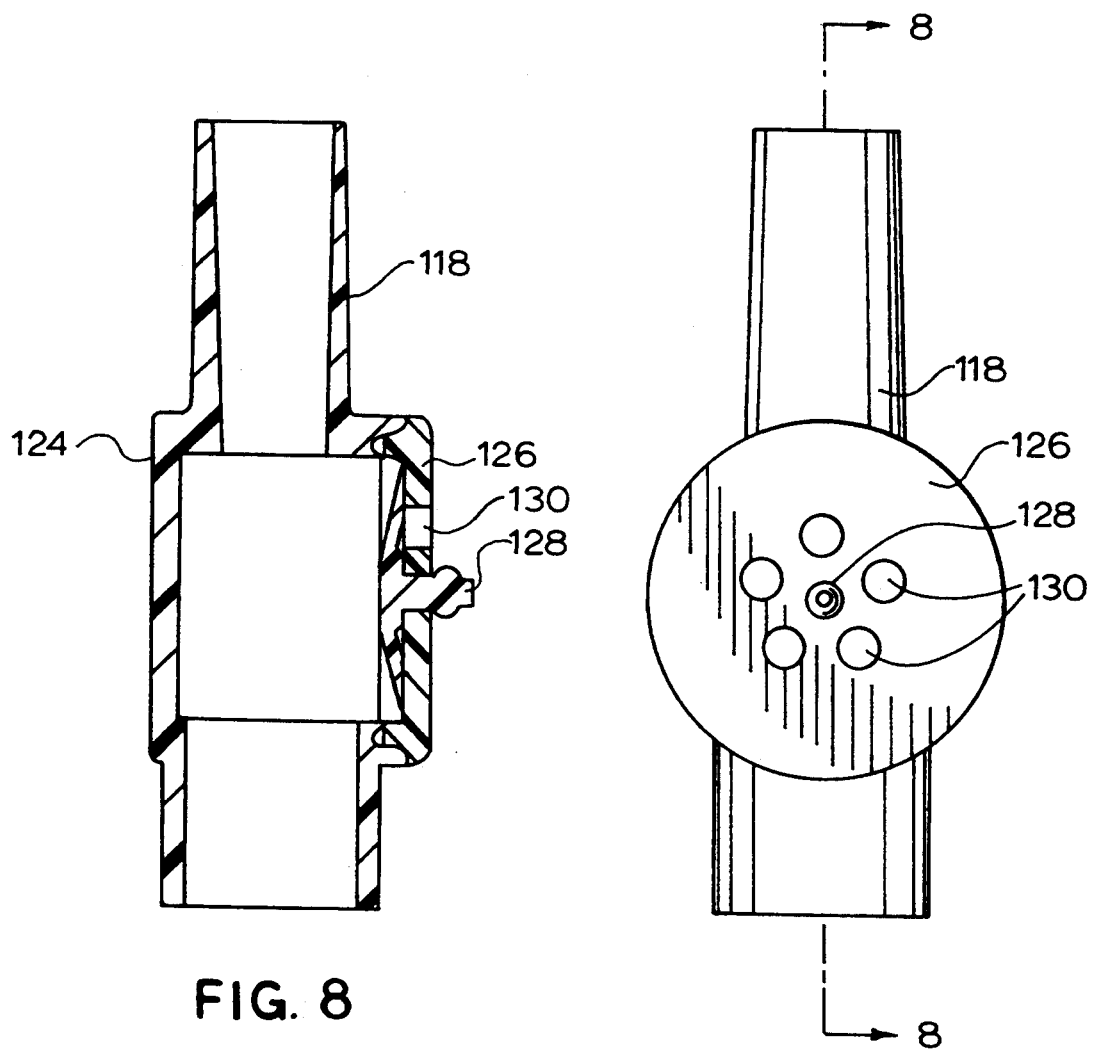
FIG. 8
FIG. 9

STAND ALONE CONTROL MODULE

FIELD OF THE INVENTION

This invention relates generally to vacuum regulating systems and one-way check valves and more specifically relates to water-based vacuum regulating systems and one-way check valves for closed-wound drainage applications.

BACKGROUND OF THE INVENTION

In the medical field it is frequently necessary after surgery or after a patient has incurred a trauma to the chest cavity to collect fluids from the chest cavity after the cavity has been closed. This type of fluid collection is commonly referred to as "closed-wound drainage". One particularly important feature of closed-wound drainage is that it requires a relatively low vacuum to suction fluids from the patient's chest cavity. If higher vacuums are used, damage to the internal organs may occur. Typical vacuum ranges of between 20–30 cm. H₂O are used to collect fluids from a closed chest or pleural cavity. However, in most hospitals, the vacuum sources commonly available are in the range of 0–760 mm. Hg. Most hospitals provide such vacuum sources on the wall next to a patient's bed. It is therefore necessary to provide a system which converts a relatively high vacuum provided by the hospital to a relatively low vacuum for use in closedwound drainage systems. It has been found that the vacuum source provided at a patient's bedside in many hospitals may also be a variable pressure vacuum source. With such sources, the vacuum provided may vary unexpectedly. Therefore, a need exists to provide a system which will not only convert a relatively high vacuum to a low vacuum but will also maintain a relatively constant vacuum despite fluctuations that may occur in the high vacuum source.

Another need exists in draining fluids and gases from a patient's pleural cavity in that it is important that as the gases are removed from a patient that they are not inadvertently returned to the patient. Typically, in a closed-wound drainage system, a small amount of gas is removed from the patient's pleural cavity with each inhalation of the patient. If the patient's lung is collapsed, each time a small amount of fluid and gas is removed from the patient's pleural cavity, the patient's lung is allowed to expand by the amount of fluid or gas that is removed. Thus, the patient's lung will typically gradually expand over a period of several days if the lung has entirely collapsed. During this process, it is important to make sure that gases are not inadvertently returned to the patient which would cause the lung to re-collapse.

Air may be inadvertently returned to a patient's pleural cavity when it is necessary to transport a patient from one location to another. When a patient is transported, it is frequently necessary to disconnect the patient from a vacuum source that is fixed in the wall of a hospital. The patient is then allowed to drain fluids from the pleural cavity using only gravity. Under such conditions, fluid will continue to drain, but air may return to the patient if air is present within the closed-wound drainage system. Therefore, it is necessary to provide a one-way check valve to prevent such return of air. One object of the present invention is to provide such a one-way check valve in a stand-alone module.

Another object of the invention is to provide a water-based stand-alone module which can be used not only for pleural wound drainage systems, but can be also be used for other drainage applications such as knee and hip surgery.

SUMMARY OF THE INVENTION

A stand-alone control module for transforming a variable high-vacuum source into a constant low-vacuum source for medical applications is described. The module also provides a one-way check valve to prohibit return of air when draining fluids and air from the pleural cavity of a patient. The module includes a first-suction control chamber for transforming a variable high-vacuum into a constant low vacuum. The first chamber contains a first column of fluid at a first pre-determined level. A second water-sealed chamber is also provided for containing a second column of fluid at a second pre-determined level. The second level is less than the first level. A lid is also provided for covering an upper surface of both the first and second chambers. The lid provides a first path between a high-vacuum source and the second chamber. The lid also provides a second path connecting the first and second chambers above the fluid levels thereby equalizing the pressure in the first and second chambers. A first tube is provided within the first chamber. The first tube has first and second ends. The first end of the first tube is immersed in the fluid in the first chamber. The second end of the first tube extends above the first chamber through the lid and is open to atmospheric pressure. Thus, when a high-vacuum source is applied to the first chamber through the second pathway, the first tube supplies atmospheric air pressure to the high-vacuum source through the first column via bubbles in the first column of fluid thereby creating a residual pressure in the first chamber which remains constant and dependent on the height of the column of fluid in the first chamber.

The module also includes a second tube within the second chamber. The second tube also has first and second ends. The first end of the second tube is immersed in the fluid in the second chamber and the second end of the tube is in communication with the pleural cavity of a patient. The vacuum in the second chamber is normally lower than the vacuum in the patient's pleural cavity. This causes air in the cavity to be pulled through the second end of the second tube through the second column of fluid towards the high-vacuum source. When the vacuum in the cavity is greater than the vacuum in the second chamber, fluid in the second chamber is pulled into the second tube to prevent air in the second chamber from returning to the pleural cavity. The second tube includes a valve located at the second end which closes when fluid rises to the second end of the tube.

BRIEF DESCRIPTION OF THE DRAWINGS

FIG. 7 is a top view of the control module;

FIG. 8 is a side view of a valve used in the preferred embodiment of the invention;

FIG. 9 is a front view of the valve illustrated in FIG. 8;

DETAILED DESCRIPTION OF THE PREFERRED EMBODIMENT

Figure 1:
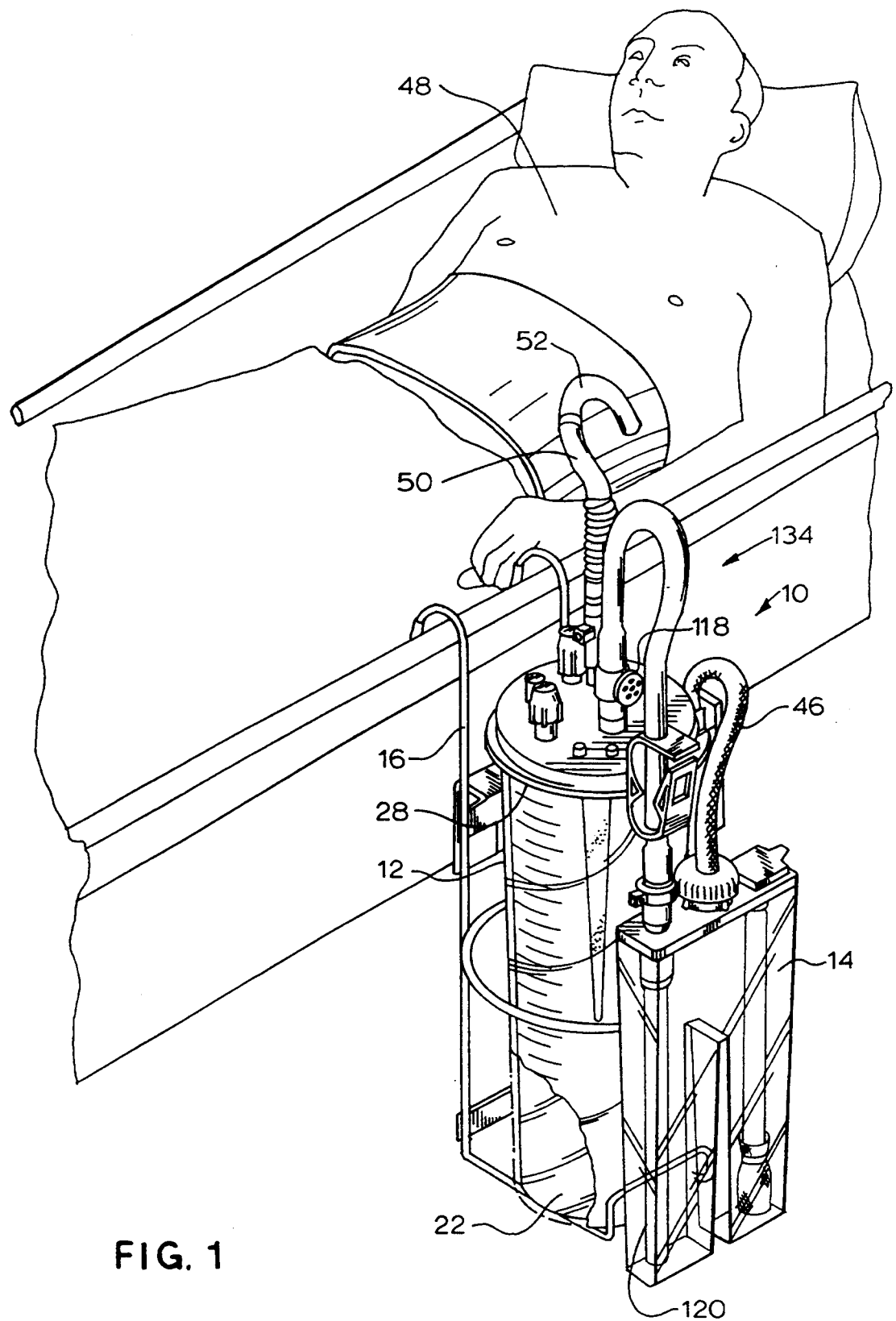
FIG. 1 is a perspective view of the preferred embodiment of a closed-wound drainage autotransfusion system.
Figure 2:
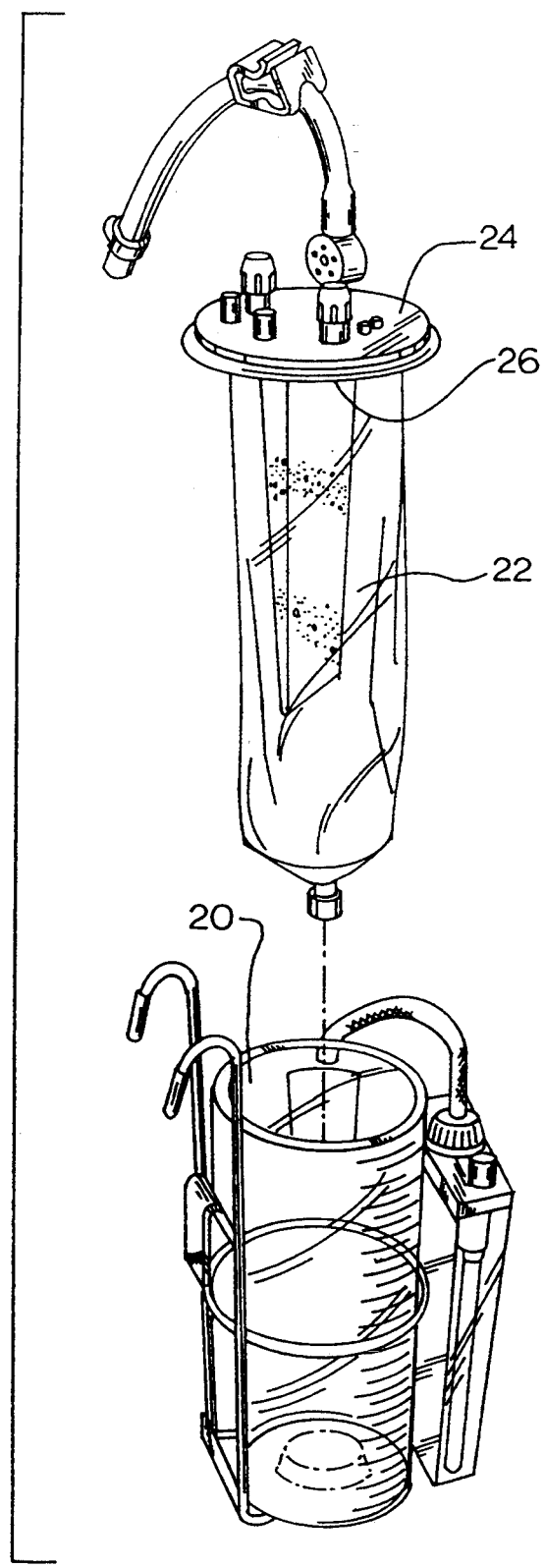
FIG. 2 is a perspective view of a liner and cannister of the preferred embodiment of the invention as the liner is inserted into the cannister.

Refer now to FIG. 1 which is a perspective view of the preferred embodiment of a closed-wound drainage autotransfusion system 10. As can be seen in the figure, the system 10 includes a cannister 12 and a control module 14. The cannister is located in a hanger 16. The control module 14 is also mounted on the hanger 16. The cannister 12 includes walls 18 which form a cavity 20 as can be seen in FIG. 2. The system includes a hollow liner 22 for insertion into the cavity 20 of the cannister. The purpose of the liner 22 is to receive fluids and gases from the pleural cavity of the patient. The liner 22 includes a cover 24 that is attached to the top 26 of the liner 22. The cover 24 and liner 22 are sealed to one another to form a fluid and gas-tight seal. The cover 24 can be attached to the top 28 of the cannister 12 as can be seen in FIG. 1.

Figure 3:
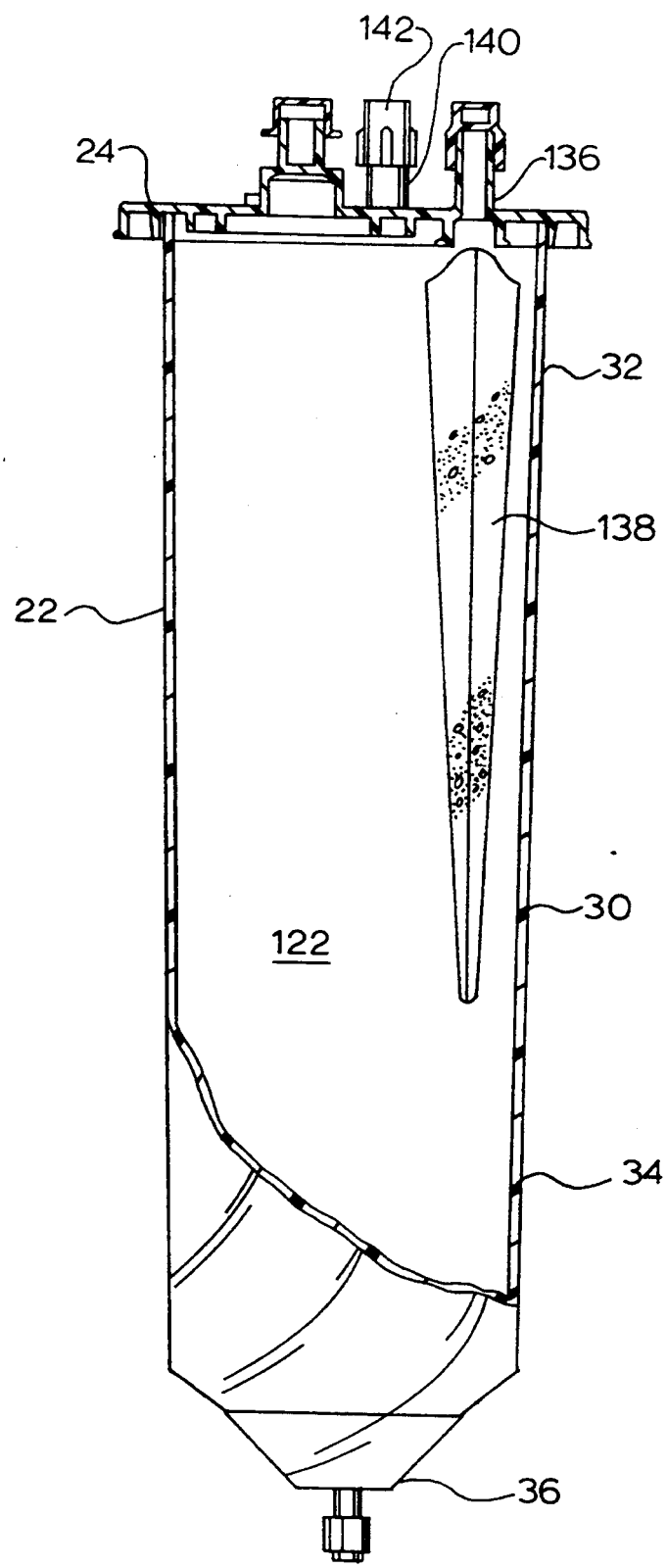
FIG. 3 is a side view of a liner.
Figure 4:
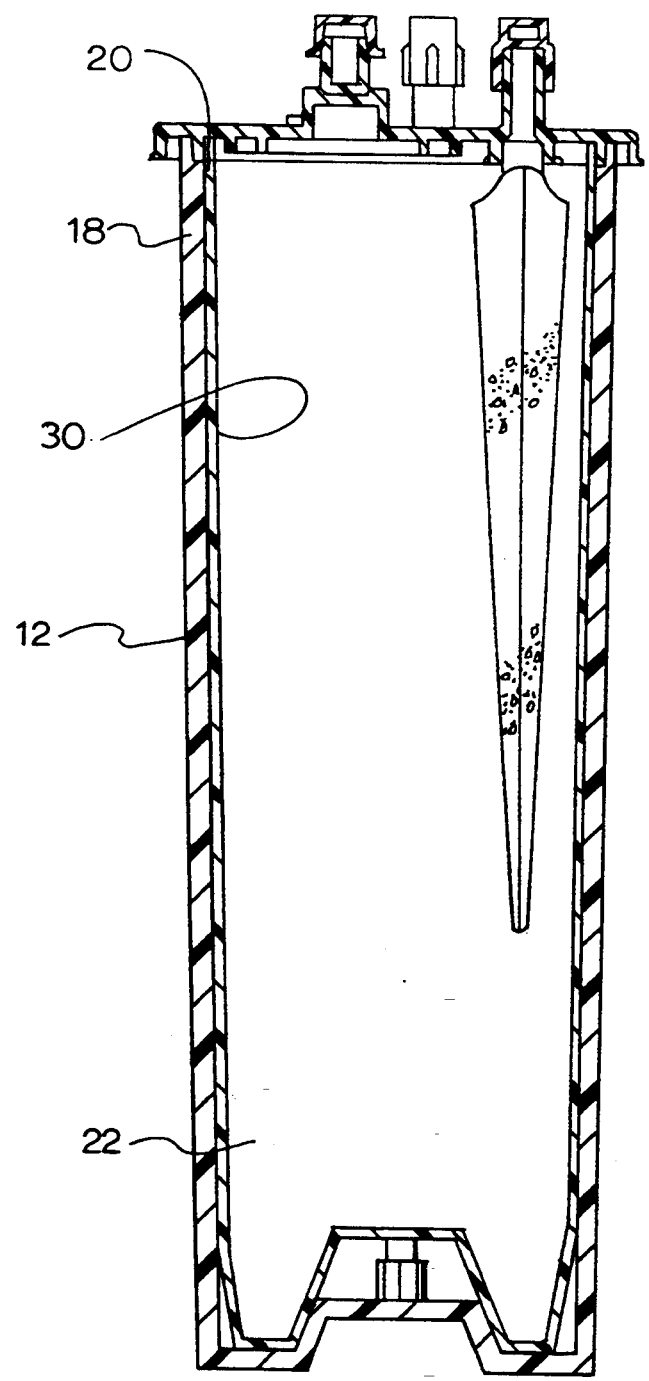
FIG. 4 is a perspective view of the preferred cannister and liner.

Referring now to FIG. 3, the liner 22 includes a flexible body 30. The flexible body 30 has upper and lower portions 32 and 34. The upper portion 32 is attached to the cover 24. The lower portion 30 is attached to a bottom 36. The flexible body 30 and the bottom 36 are shaped so as to generally conform to the walls 18 of the cannister 12. Therefore, when the flexible body 30 and the bottom 36 are inserted into the cavity 20 as illustrated in FIG. 2, the liner 22 will fit snugly against the walls 18 of the cavity 20 of the cannister 12 as illustrated in FIG. 4.

Figure 5:
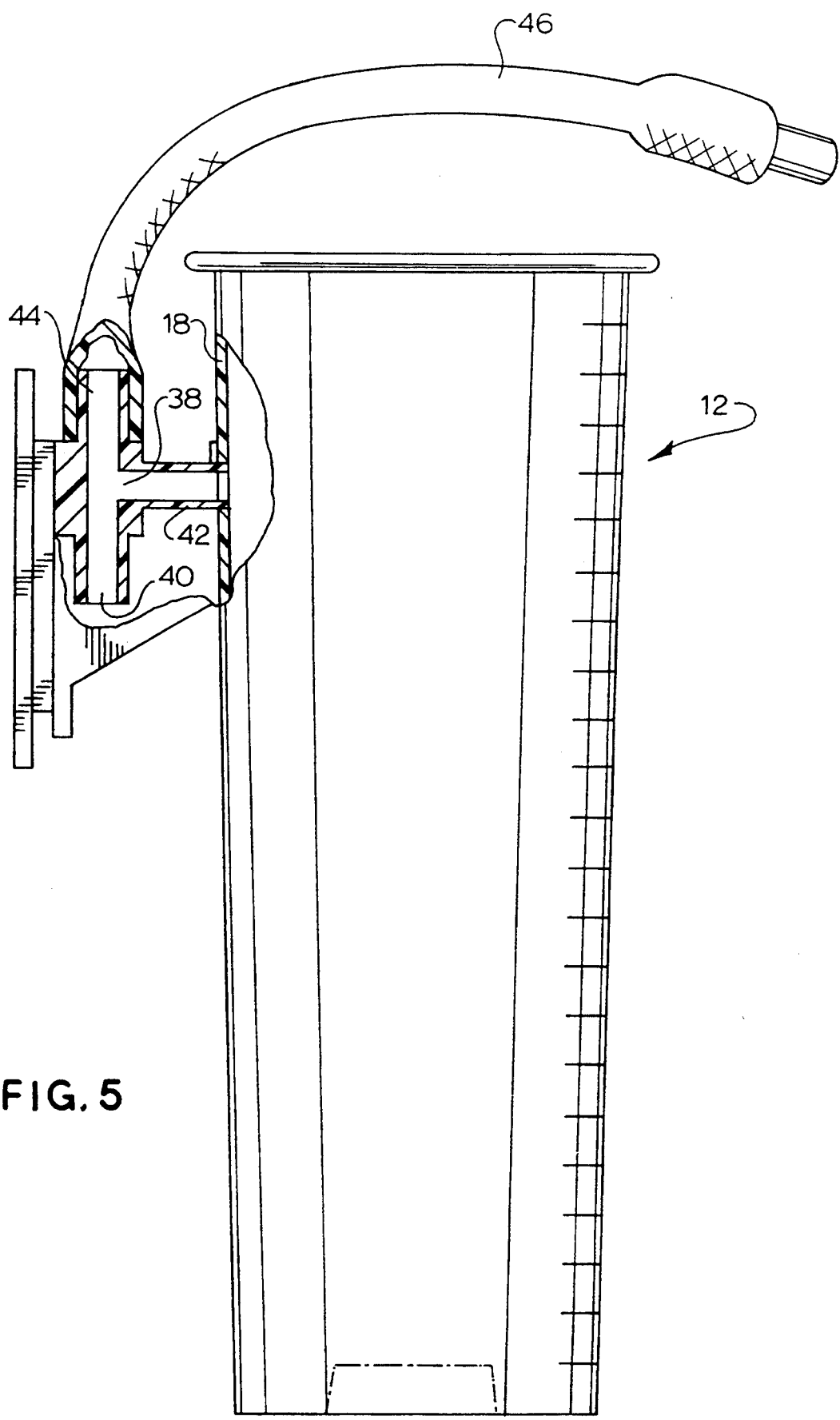
FIG. 5 is a perspective view of a re-usable cannister showing a vacuum connection to the cavity of the cannister.

In the preferred embodiment, the system 10 includes a vacuum means for continuously providing a relatively high vacuum to the cavity 20 of the cannister 12 and a relatively low vacuum inside the liner 22 when the liner 22 is located in the cavity 20 to cause the liner to expand against the walls 18 of the cannister 12. The vacuum means includes a "T"-shaped port 38 as illustrated in FIG. 5. The port 38 includes a lower leg 40 which can be connected to a high-vacuum source. The high-vacuum source is typically a vacuum-source provided in the wall of a hospital next to a patient's bed. In many hospitals, this source of high-vacuum tends to provide a vacuum in the range of 0–760 mm. Hg. This vacuum may vary unexpectedly. However, the vacuum is generally sufficient to cause the flexible body 30 to expand against the walls 18 of the cannister 12 when the vacuum is applied through a middle leg 42 of the "T"-shaped port 38. The middle leg 42 is in fluid communication with the cavity 20 of the cannister 12 to allow the high vacuum source to be applied to the cavity 20. The "T"-shaped port 38 also includes an upper leg 44 which is attached to a braided tube 46 which will be discussed in greater detail below.

The vacuum means which provides a relatively low vacuum to the inside of the liner 22 must provide this vacuum at a constant relatively low level. The reason why the vacuum provided to the inside of the liner 22 must remain constant is that variations in the vacuum in the liner are transmitted to the patient 48 via a drainage tube 50 which is connected to a chest tube 52 as illustrated in FIG. 1. Thus, if a high vacuum is applied to the inside of the liner 22 the same vacuum will be applied to the chest cavity of the patient 48. This can injure the patient's internal organs. Also, variations in vacuum can injure the patient's organs even if the vacuums are relatively low. Therefore, the high vacuum present in braided tube 46 is transmitted into control module 14 for transforming the variable high vacuum into a constant low vacuum. The control module 14 is illustrated in greater detail in FIG. 6.

Figure 6:
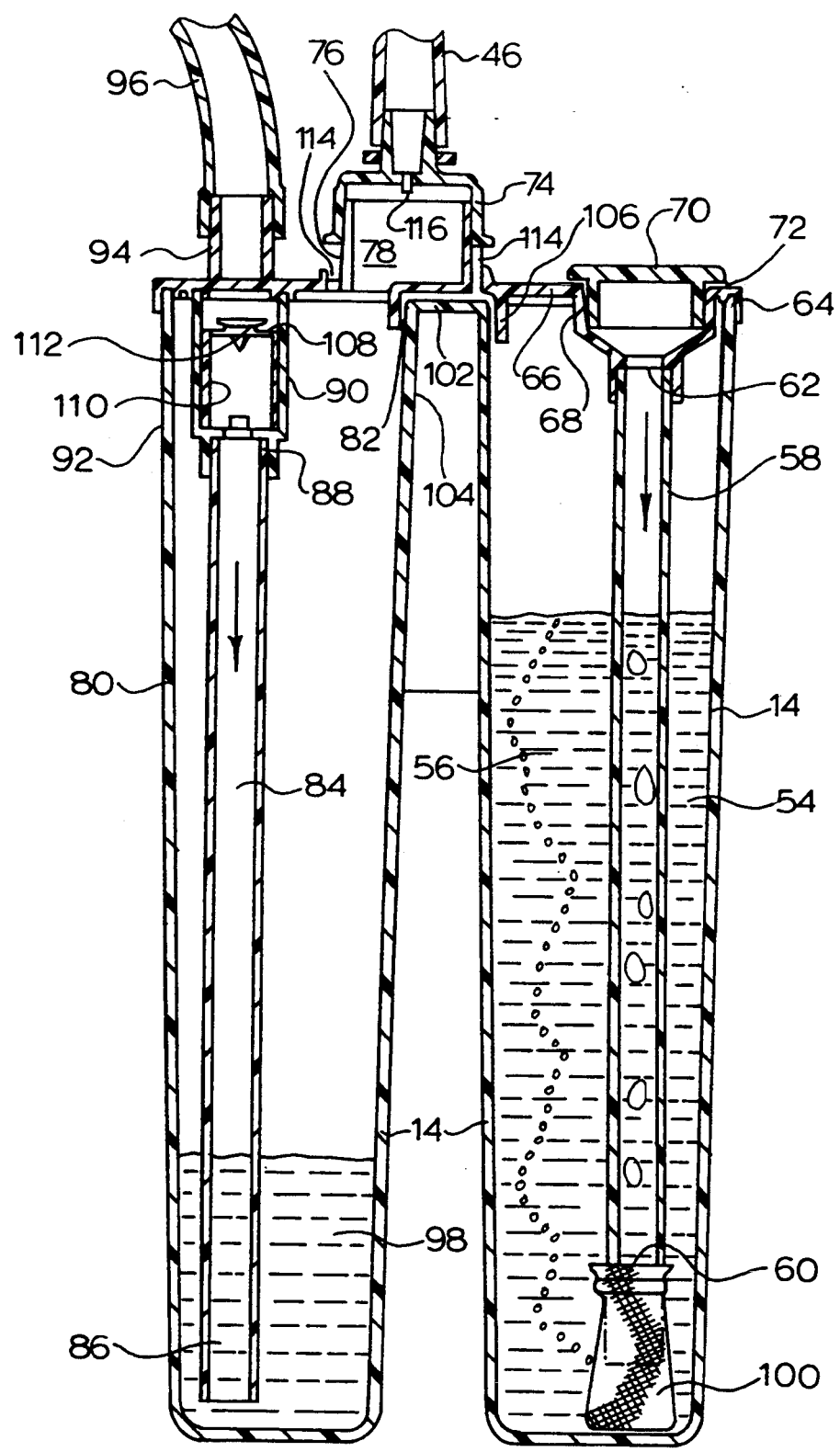
FIG. 6 is a cut-away view of the control module taken along lines 6—6 in FIG. 7.

As can be seen in FIG. 6, the control module 14 includes a first suction control chamber 54 for transforming the variable high vacuum into a constant low vacuum. When the module 14 is in use, the chamber 54 is partially filled with a sterile fluid 56. The first chamber 54 include a first tube 58 that is located within the first chamber 54. The first tube has first and second ends 60 and 62. The first end 60 is the immersed in fluid 56 and the second end 62 extends above the top of the fluid 56 in the first chamber. The second end 62 is attached to a lid 66 which covers the top 64 of the first chamber 54. The lid 66 includes a port 68 which is located immediately above the top 64 of the first chamber 54. The second end 62 of the first tube 58 is in sealed engagement with the port 68. The port is partially covered by a cap 70. A narrow air space 72 exists between the cap 70 and the port 68 to allow atmospheric air pressure into tube 58. The high-vacuum source present in braided tube 46 is attached to a cap 74 which is located on a high-vacuum port 76 on lid 66. The port 76 provides a first path 78 between the high-vacuum source and a second chamber 80 in the control module 14. The lid 66 and the control module 14 are shaped in such a way that when the lid 66 is placed on the control module 14 a second path 82 is formed between the first and second chambers 54 and 80. The second path is a relatively narrow path that provides fluid communication between the first and second chamber 54 and 80. Thus, the high vacuum provided to the second chamber 80 through port 76 is also transmitted to the first chamber 54. The high vacuum causes atmospheric air present in tube 58 to be pulled through the first end 60 of the tube against the first column 56 of fluid. The resistive force of the water pressure against the air as it is drawn through the water column creates a relatively low back pressure which is proportional to the height of the column of water. This reduces the vacuum present in the upper portion of the chamber 54 to a relatively low, constant vacuum which can be controlled simply by controlling the height of the column of fluid. Therefore, the first chamber 54 acts as a pressure regulator which transforms a variable high vacuum into a constant relatively low vacuum.

The control module 14 includes a second chamber 80 which provides a water-based one-way check valve. This chamber will now be discussed in greater detail. The chamber 80 includes a second tube 84 which is located within the chamber. The second tube 84 includes first and second ends 86 and 88. The first end 86 is immersed in sterile fluid when the module 14 is in use. In the preferred embodiment, the second chamber 80 is partially filled with 2 cm. high of sterile fluid. The second end 88 of the second tube 84 is attached to a vacuum-interface port 80 on lid 66. The vacuum-interface port 80 is located over the upper portion 82 of the second chamber 80. The vacuum-interface port 80 has one end 84 connected to a vacuum-interface tube 86 which will be discussed in greater detail below. The vacuum-interface tube 86 is in fluid communication with the inside of the liner 22. As discussed above, the vacuum present within the liner 22 is in fluid communication with the cavity of a patient 48 through tubes 50, 52. Therefore, the vacuum present in the first and second chambers 54, 80 of the control module 14 is also the same vacuum that is provided to the cavity of the patient 48.

The purpose of the second chamber 80 of the control module 14 is to provide a one-way fluid-based check valve to prevent gases from being delivered to the cavity of a patient 48. As will be discussed in greater detail below, gases are allowed to travel downwardly through the second tube 84, but are not allowed to travel from the upper portion 82 of the second chamber 80 through tube 84. As discussed above, the second chamber 80 includes a second column of fluid 88 which is 2 cm. high in the preferred embodiment of the invention. The second column of fluid 88 acts to prevent gas present in the upper portion 82 of the second chamber 80 from entering the first end 86 of the second tube 84 in the event that the pressure in the upper portion 82 of the second chamber 80 is greater than the pressure in the patient's cavity. The pressure in the upper portion 82 of the second chamber may be greater than the pressure in the patient's cavity when the system 10 is disconnected from a high-vacuum source. In this event, the pressure and the upper portion 82 of the second chamber 80 will rise to atmospheric pressure. If fluid is not present in the second chamber 80, this atmospheric pressure can be transmitted too the patient's cavity causing the patient's lung to collapse. This is prevented by the presence of a second column of fluid 88 and the second chamber 80. When the pressure in the upper portion 82 of the chamber 80 is greater than the pressure in a patient's cavity, each exhalation of the patient will cause the fluid in the second chamber 80 to be drawn up into the second tube 84 temporarily. The fluid that is drawn up into the second tube 84 rises and falls with each patient inhalation and exhalation whenever the system 10 is disconnected from a high-vacuum source. This fluid in the second tube 84 prevents any gas present in the second chamber from entering into the patient's chest cavity.

One feature of the control module 14 is that the first tube 58 includes a mesh net 100 covering the first end 60 of the first tube 58. The purpose of the mesh net 100 is to cause air drawn through the first tube 58 into the first column 58 of fluid to be broken up into very fine bubbles. This act of breaking the air into fine bubbles reduces turbulence in the first column 56 of fluid. This is important because it prevents splashing of fluid 56 in the first chamber into the second chamber 80 through the second path 82.

As discussed above, the lid 66 and the upper portion 102 of the control module between the first and second chambers 54, 80 forms the second path 82. In the preferred embodiment of the invention, the lid 66 and the upper portion 102 of the control module 14 form a gap with one another that creates the second path 82. The entrance to the second path 82 from the first chamber 54 in the preferred embodiment is no greater than 0.06 inches. The purpose of providing a very small entrance to the second path 82 from the first chamber 54 is to reduce the possibility of fluid 56 in the first chamber 54 from entering the second chamber 80. In the preferred embodiment, the second path 82 is a narrow torturous path. As illustrated in FIG. 6, the path 82 is a "U"-shaped path formed by "U"-shaped portion 104 in the upper portion 102 of the control module 14 which is parallel to a "U"-shaped portion 106 in lid 66.

As also illustrated in FIG. 6, the second end 88 of the second tube 84 is attached to a vacuum-interface port 80. A float valve 108 is located inside the port 80. The float valve 108 includes an inverted rubber cup 110 which is centered over the upper end 88 of the second tube 84. As fluid in the second tube 84 reaches the inverted cup 110, the cup rises until a flexible gasket 112 located between the upper portion of the cup 110 and the vacuum-interface port 84 causes the float valve 108 to close.

One important feature of the preferred embodiment of the invention is that the lid 66 includes at least one bleed orifice 114. In the preferred embodiment of the invention, a bleed orifice 114 is located adjacent to the first path 78 on the lid 66. The purpose of the bleed orifice 114 is to transform the high-source vacuum into an intermediate level vacuum which can be further reduced to a low vacuum by the first chamber 54 of the control module 14. By allowing small amounts of air to enter into the first and second chambers 54, 80 through the bleed orifice 114, the vacuum from the high-vacuum source is partially reduced.

The high vacuum from the high-vacuum source is also partially reduced through the use of an in-line orifice 116 located in the high-vacuum cap 74. The relatively small in-line orifice 116 causes the high vacuum from the high-vacuum source to be reduced to a lower vacuum since the bleed orifice 114 pulls air into the upper portions of the first and second chambers as a high vacuum is applied to the inline orifice 116. Therefore, the in-line orifice 116 and the bleed orifice 114 act in conjunction to produce an intermediate level vacuum which is then reduced to a low vacuum as discussed above.

In the preferred embodiment of the invention, the first column of fluid 56 in the first chamber 54 is formed using no greater than 220 cc of fluid to provide 20 cm. $H_2O$ vacuum in the first and second chambers 54, 80 when the high-vacuum source provides up to 14.7 psi vacuum to the first path 78. This is a relatively small amount of fluid compared to other systems used in the past. This small amount of fluid is able to provide a reduction in vacuum due to the use of the bleed orifice 114 and the in-line orifice 116 to step down the vacuum from the high-vacuum source to an intermediate level vacuum.

Refer again to FIG. 1, as can be seen in this figure in the preferred embodiment of the invention, a vacuum-sensing valve 118 is provided in series between the low-vacuum source 120 of the control module 14 and the inside 122 of the liner 22. The valve is designed to open the inside of the liner to atmospheric pressure when the vacuum inside 122 the liner 22 exceeds a pre-determined value. In the preferred embodiment of the invention, the pre-determined value is 40 cm. $H_2O$. This prevents undesirably high vacuums from being applied to the patient's chest cavity. The valve 118 will now be described in greater detail. Refer now to FIG. 8, which is a cut-away view of the vacuum-sensing valve 118.

The valve includes a valve body 124, a seat 126 and an elastomeric umbrella 128. As can be seen in FIG. 8, the seat 126 of the vacuum-sensing valve 118 includes a plurality of openings 130 to allow atmospheric air to enter the valve body 124 when the vacuum within the valve body exceeds a pre-determined level. When the vacuum exceeds this pre-determined level, the edges 132 of the elastomeric umbrella 128 will be drawn toward the center of the valve body 124 and away from the valve seat 126. When the edges 132 of the elastomeric umbrella 128 are in their normal position, the edges 132 are biased against the openings 130. However, when the vacuum exceeds the pre-determined level, as discussed above, the edges will withdraw into the valve body 124 to allow atmospheric air into the valve body. This prevents undesirably high vacuums which may be present inside the liner 122 to be applied to the chest cavity of a patient.

Refer now to FIG. 1. One important feature of the invention is that the system 10 includes a drainage means 134 for providing fluid communication between the inside of the liner 122 and the chest cavity of the patient 48. In the preferred embodiment of the invention, the drainage means 134 includes a drainage tube 50 which is connected to a patient port 136 and the cover 24 of the system 10. The patient port 136 has a porous filter 138 attached to collect large particle-size debris which may be drawn into the system from the patient's chest cavity. This filter prevents this degree from being mixed with fluid that is collected in the liner 22 for later re-infusion back into the patient. In the preferred embodiment of the invention, the filter has a pore size of between 120 and 130 microns. The filter is located inside the liner 22 immediately under the patient port 136.

Figure 10:
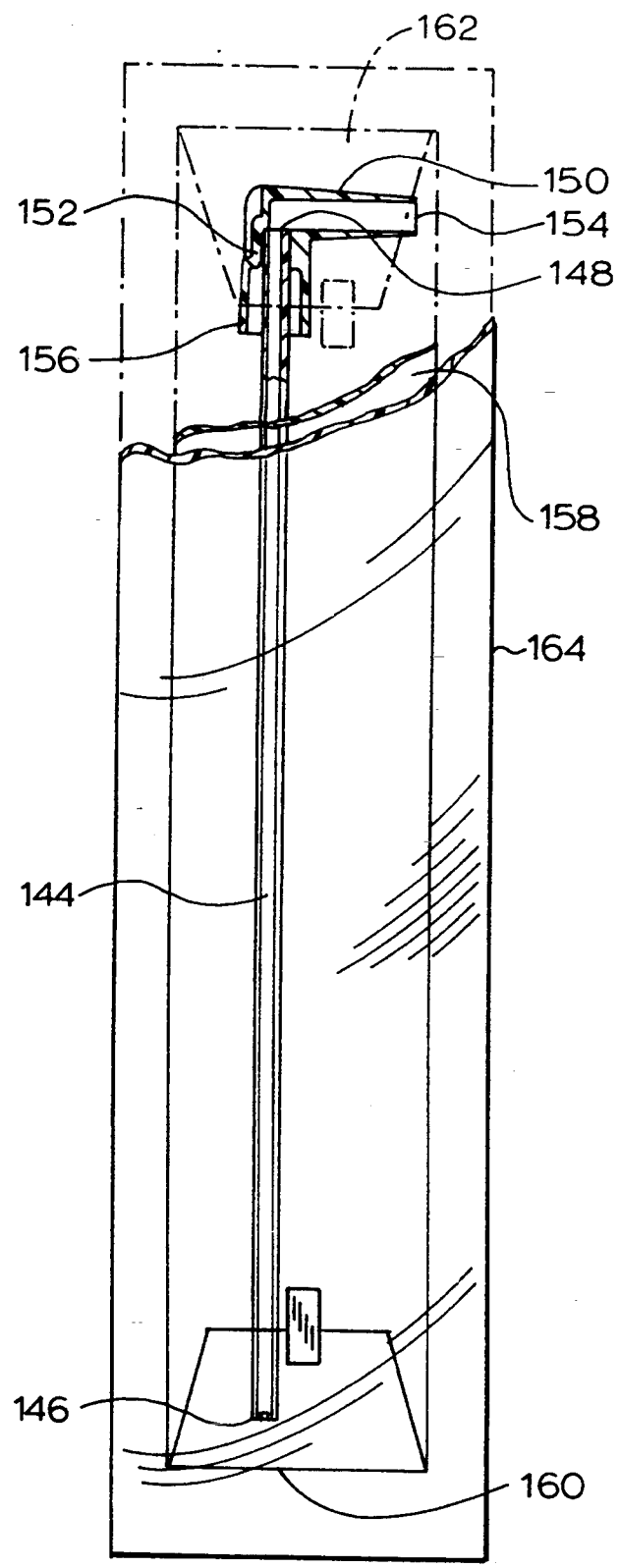
FIG. 10 is an illustration of a drainage straw used in one embodiment of the invention.

In the preferred embodiment of the invention, the cover 24 also includes an interface port 140 to allow removal of fluids from the liner 22 for further processing or re-infusion back into the patient without removing the liner from the cannister. When the interface port 140 is not in use, the port is covered with a cap 142. In the preferred embodiment of the invention, a sterile straw 144 is inserted into the liner 22 to withdraw fluids from the bottom of the liner. The straw is illustrated in FIG. 10 in its pouch.

The straw 144 has first and second ends 146, 148. The first end of the straw can be inserted through the interface port 140 down into the bottom of the liner 22. The second end 148 of the straw 144 is attached to an elbow 150. The elbow includes first and second ends 152, 154. The first end of the elbow includes a skirt 156 which is designed to fit snugly around the outside diameter of the interface port 140 to firmly secure the straw onto the interface port 140. Accordingly, the skirt 156 consists of a ring which can be concentrically placed about the interface port 140. The second end 154 of the elbow 150 has a tapered port for connection to tubing of various inside diameters. This port is normally attached to such tubing to allow fluid within the liner to be drawn into the tubing either for re-infusion back into the patient or for further processing. For example, in some instances, it may be desirable to sent the fluid through a cell washer to remove the red cells from the fluid and discard any other debris that may be present in the fluid. The red cells may then be used by the patient.

Thus, it is important for the straw 144 to be maintained in a sterile condition prior to insertion into the liner 22, It is also important that the medical personnel be able to insert the straw 144 into the liner 22 without compromising its sterility. Therefore, one feature of this invention is to provide a sterile system in which the straw is maintained in a sterile, thin-walled flexible sleeve 158 prior to insertion into the liner 22. As can be seen in FIG. 10, the sleeve completely covers the straw. The sleeve has first and second ends 160 and 162. In the preferred embodiment, the ends are simply folded inward towards the sleeve and taped shut. In one embodiment of the invention, medical personnel can open the first end 160 of the sleeve 158 to expose the first end 146 of the straw 144. The first end 160 of the sleeve 158 can be pushed back toward the elbow to allow the first end 146 of the straw 144 to be inserted into the liner 22 while the second end 148 of the straw remains covered by the sleeve 158. After the straw has been inserted, the sleeve can be completely removed to allow the second end 154 of the elbow 150 to be attached to a tube as discussed above. In another embodiment of the invention the first end 160 of the sleeve 158 is opened simply by forcefully puncturing the sleeve with the first end 146 of the straw 144.

In order to insure that the straw 144 is transported in a sterile condition, the entire sleeve 158 is enclosed in an outer peelable outer pouch 164. The outer pouch can be opened by a "non-sterile" medical personnel to present the sterile sleeve 158 and straw 144 to a "sterile" nurse.

Figure 11:
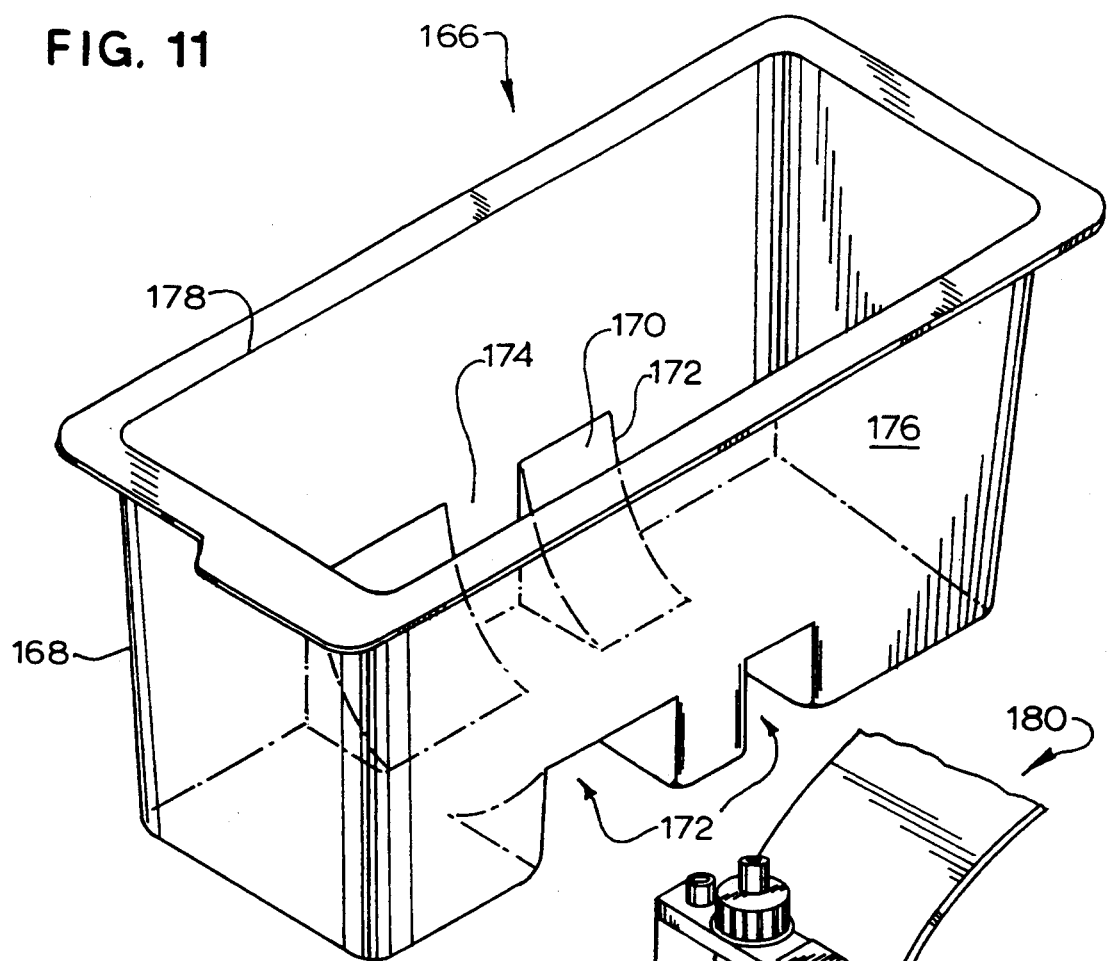
FIG. 11 is a perspective view of a tray for storing and transporting a control module.
Figure 12:
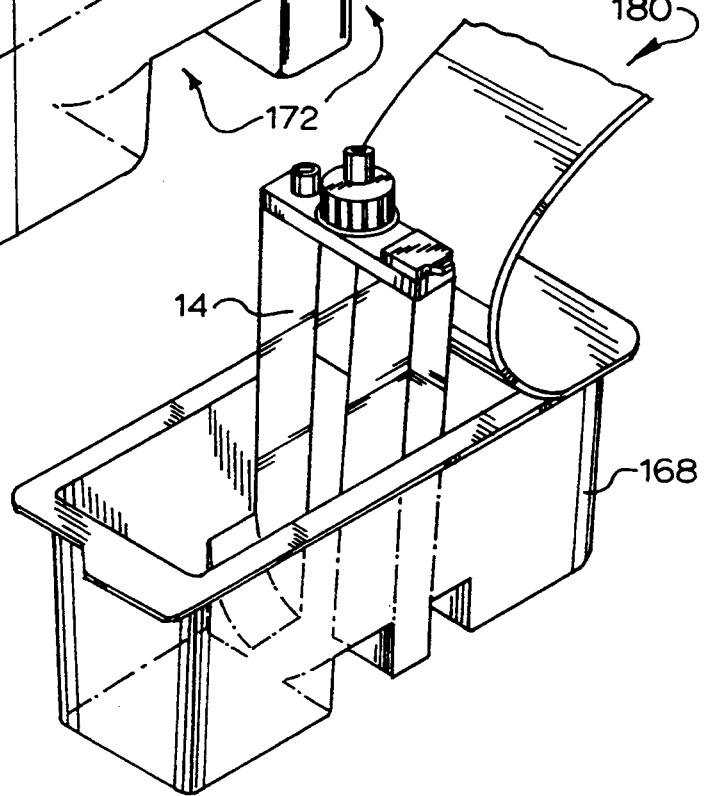
FIG. 12 is a perspective view of a control module located in the tray of FIG. 11 in the upright position to allow fluid to be added to the control module.

Refer now to FIG. 11 which is a perspective view of a tray 166 used to store and transport the control module 14. The tray 166 includes a storage means 168 for maintaining the control module 14 in a horizontal position within the tray as the module is being transported. The tray 166 also includes a holding means 170 for maintaining the control module 14 in a vertical position in the tray 168 to allow the control module 14 to be partially filled with sterile fluid. This is illustrated in FIG. 12. In the preferred embodiment of the invention, the holding means includes a pair of indentions 172 which form a slot 174 for maintaining the control module 14 in a vertical position. In the preferred embodiment, the storage means 168 is a pre-formed plastic container 176 having a top opening 178 that is sealed with a lid 180 which can be peeled away from the top opening to expose the inside of the container 176. In the preferred embodiment, the preformed container 176 includes a bottom and side walls which generally conform to the overall outer shape of the control module 14 when the control module 14 is in a horizontal position. Thus, the control module 14 can be snugly placed inside the container 176 to be transported.

The tray 166 described herein has several advantages. First, the use of the tray to maintain the control module in an upright position as the module is being filled acts as a sterile field around the control module since the inside of the tray is sterile prior to peeling back the lid 180 from the top 178 of the tray. Second, the tray 166 acts as a fluid collection means to collect any spills which may occur as the module is being filled. This is of great value to operating room personnel.

I claim:

1. A stand-alone control module for transforming a variable high vacuum source into a constant low vacuum source for medical applications and for providing a one-way check valve to prohibit return of air when draining fluids and air through a drainage tube having a first end located in the plural cavity of a patient comprising:

a first chamber containing a first column of fluid having a height at a first predetermined level;

a second chamber containing a second column of fluid at a second predetermined level, said second level being less than said first level;

a lid covering an upper surface of both of said first and second chambers, said lid having a first port for connecting said second chamber to a high vacuum source, said lid providing a connecting pathway connecting said first and second chambers above said fluid levels in said first and second chambers thereby equalizing a pressure differential between said first and second chambers, a first tube within said first chamber, said first tube having first and second ends, said first end of said first tube being immersed in said first column of fluid and said second end of said first tube extending above said first chamber through said lid and being open to atmospheric pressure, whereby when said high vacuum source is applied to said first chamber through said connecting pathway, said first tube supplies atmospheric air to said first chamber through said first column of fluid via bubbles thereby creating a residual pressure in said first chamber which remains constant and dependent on the height of said first column of fluid in said first chamber, said first end of said first tube having a mesh net covering said end to break up air in said tube into fine bubbles before entering said first fluid column to reduce turbulence and noise in said first chamber; and a second tube within said second chamber, said second tube having first and second ends, said first end of said second tube being immersed in said second column of fluid in said second chamber and said second end of said second tube being connected to said second end of said drainage tube to be in communication with the plural cavity of the patient, said second chamber having a vacuum which is normally lower than a vacuum in the patient's pleural cavity thereby causing air in the pleural cavity to be pulled through said second end of said second tube through said second column of fluid toward said high vacuum source, when said vacuum in said pleural cavity is greater than vacuum in the second chamber, fluid in said second chamber is pulled into said second tube to prevent air in said second chamber from returning to said pleural cavity, said second tube having a valve located at said second end which closes when said second fluid column rises to said second end of said tube.

2. A control module as recited in claim 1 wherein said first port in said lid further includes a cap having an air flow restrictor between said first path and said high vacuum source to cause a drop in vacuum between said high vacuum source and said second chamber, said lid also having at least one bleed orifice to atmosphere and at least one of said first and second chambers, said bleed orifice also causing an additional drop in vacuum in said chambers to prevent excessive bubbling in said first chamber when said high vacuum source is providing maximum vacuum.

3. A control module as recited in claim 2 wherein said bleed orifice is located adjacent said first port on said lid.

4. A control module as recited in claim 1 wherein said valve is a float valve having a rubber gasket surrounding said second wherein said valve seals said second end of said second tube when fluid in said second tube rises to said second end.

5. A control module as recited in claim 1 wherein said connecting pathway between said first and second chambers in said lid is a narrow torturous pathway to prevent fluid in said first chamber from splashing into said second chamber.

6. A control module as recited in claim 5 wherein said connecting pathway has an entrance into said first chamber of no greater than 0.060".

7. A control module as recited in claim 5 wherein said connecting pathway has an entrance into said first chamber of between 0.040" and 0.125".

8. A control module as recited in claim 1 wherein said mesh net has a mesh openings in the range of 0.010" to 0.015".

9. A control module as recited in claim 1 wherein said first fluid column is formed using no greater than 220 cc of fluid to provide 20 cm $H_2O$ vacuum in said first and second chambers when said high vacuum source provides up to 14.7 psi vacuum to said first path.

* * * * *